United States Patent [19]

Seckinger

[11] 4,334,738
[45] Jun. 15, 1982

[54] METHOD OF PERIMETRIC EXAMINATION OF VISUAL FIELDS

[75] Inventor: Erich Seckinger, Dübendorf, Switzerland

[73] Assignee: Interzeag AG, Schlieren, Switzerland

[21] Appl. No.: 933,851

[22] Filed: Aug. 15, 1978

[30] Foreign Application Priority Data

Sep. 9, 1977 [CH] Switzerland ................. 11059/77
Sep. 9, 1977 [CH] Switzerland ................. 11060/77

[51] Int. Cl.³ .................... A61B 3/02; A61B 3/00
[52] U.S. Cl. ................................... 351/39; 351/23
[58] Field of Search ............. 351/23, 24, 35, 36, 351/39

[56] References Cited

U.S. PATENT DOCUMENTS 3,664,732  5/1972  Lynn .......................... 351/24 X
3,718,386  2/1973  Lynn et al. ................... 351/23 X
4,145,123  3/1979  Krahn et al. .................. 351/23 X

OTHER PUBLICATIONS

Bedwell, American Journal of Optometry and Archives of American Academy of Optometry, 10/67.

*Primary Examiner*—John K. Corbin
*Assistant Examiner*—Rodney B. Bovernick
*Attorney, Agent, or Firm*—Kontler, Grimes & Battersby

[57] ABSTRACT

A method of static perimetric examination of the visual field of a subject involves presenting to the subject a plurality of spots of light of predetermined stimulus values which constitute a group of statistically ascertained mean thresholds for the age group of the subject. Such light spots are presented in a test field in accordance with a randomly selected pattern which is determined by a computer. The computer records the threshold value of each spot and modifies the corresponding stimulus value of the group by replacing it with the threshold value. The modified group is used for presentation of light spots to the same subject during a future test. The threshold values which are obtained in the course of the next-following test are processed by the computer in such a way that the computer replaces each stimulus value of the modified group with the freshly ascertained threshold value if the stimulus value of the modified group does not constitute a perimetrically ascertained threshold value; otherwise, the computer records a value which represents the arithmetic mean between the freshly ascertained threshold value and the corresponding stimulus value of the modified group. The computer further ascertains additional threshold values by interpolation, and the interpolated threshold values replace the corresponding stimulus values of the original group or are replaced with the corresponding stimulus values of the modified group if such stimulus values represent perimetrically ascertained thresholds.

10 Claims, 10 Drawing Figures

METHOD OF PERIMETRIC EXAMINATION OF VISUAL FIELDS

BACKGROUND OF THE INVENTION

The present invention relates to a method of testing visual fields of the eyes of subjects. More particularly, the invention relates to improvements in a method of examining the visual field of a subject with a perimeter machine, e.g., a machine known as "OCTOPUS" (trademark) distributed by HITRON Corporation, Norwood, N.J.

The automated perimeter machine of HITRON is equipped with a computer and an external memory. A subject who is seated in front of a cupola which defines an illuminated test field is presented a group of stimuli of variable intensity in a sequence which is determined by the computer or by the external memory. The threshold values of the group of stimuli which acted as stimuli to the subject, i.e., which were barely perceived by the subject, are recorded and stored for further reference during the next examination. The first value of each stimulus of the group corresponds to that value which is stored in the external memory. Such first value is normally chosen to correspond to the mean threshold for the respective age group and the selected region of the visual field.

Automatic testing of the visual field normally involves the subdivision of a two-dimensional area into a series of equidistant points which together constitute a lattice or raster. The raster is oriented transversely with reference to a predetermined direction, namely, the direction of gaze. The subject is thereupon presented stimuli at points which are selected at random and the intensity of stimuli is varied, preferably by resorting to the so-called repetitive bracketing strategy (also called staircase or up-and-down method) which leads to greater accuracy in determining the threshold. The threshold value of a stimulus is reached when the subject perceives the stimulus with a 50 percent probability. The reason for starting with a stimulus having a mean threshold for the age group of the subject to be tested is to reduce the number of presentations of stimuli of varying intensity at a given point before the subject perceives the stimulus having the desired threshold value. The aforementioned bracketing strategy also contributes to rapid determination of the threshold values of stimuli for all selected points of the raster.

Automatic programmed perimetry is known for several years. Such automatic mode of perimetric examination enables an ophthalmologist to follow the progress of a disease (or the effectiveness or lack of effectiveness of treatment) on the basis of several tests at regular or irregular intervals, e.g., at intervals of several weeks or months. A drawback of presently known perimetric examination techniques is that the comparison of tests made at timely spaced intervals requires much time and experience. In other words, the task of ascertaining and evaluating differences between the results of successive examinations is a lengthy procedure which must be carried out by a highly skilled physician.

The following prior art publications relate to the field of the present invention: "Octopus-an automated perimeter" (article by J. Spahr and F. Frankhauser in Review of Sensory Disability, No. 18, 1974, pp. 5–8): "Automatisierung der Perimetrie" (article by J. Spahr and F. Frankhauser in Opththalmologica, Basel, No. 170, 1975, pp. 106–107); "Fortschritte in der Automatisierung der Perimetrie" (article by J. Spahr, F. Frankhauser and H. Bebie in Klin. Mbl. Augenheilk., No. 168, 1976, pp. 84–86); U.S. Pat. No. 3,664,732 granted May 23, 1972 to J. R. Lynn.

OBJECTS AND SUMMARY OF THE INVENTION

An object of the invention is to provide a novel and improved method of testing the visual field of a subject which contributes to convenience and shortening of repetitive perimetric examination.

Another object of the invention is to provide a method which facilitates the interpretation of records of repeated perimetric examination.

A further object of the invention is to provide a method which facilitates the estimation of significance of changes in a visual field which is measured at intervals of days, weeks or months.

An additional object of the invention is to provide a novel method of altering the records of previous perimetric examinations on the basis of next-following examinations.

Another object of the invention is to provide a method which automatically furnishes information pertaining to changes in a visual field between two successive perimetric examinations and which furnishes such information with a high degree of accuracy.

The invention is embodied in a method of testing the visual field of a subject by resorting to perimetric examination, especially a static perimetric examination. The method comprises the steps of selecting a group of stimulus values to be presented to a subject (preferably a group consisting of stimulus values each of which represents the mean threshold for the age group of the subject), presenting to the subject spots of light of predetermined stimulus values of such group at different (preferably randomly selected) test locations on a test field which is properly oriented relative to the subject's direction of gaze, recording the threshold values which acted as stimuli to the subject, modifying at least some stimulus values of the group as a function of the corresponding threshold values, and storing the thus modified stimulus values of the group for presentation to the same subject during a future test. Thus, instead of starting a future test with a group of stimulus values which represent the mean threshold for the age group of the subject, such future or next-following test can be started by presenting to the subject spots of light of modified stimulus values obtained in the course or as a result of preceding examination of the same subject.

The method may further comprise the step of interpolating additional stimulus values between the recorded threshold values, and modifying the corresponding values of the group as a function of such interpolated values. This renders it possible to determine the sensitivity of the subject's eye over the whole area, with resort to a mathematical approximation, by the simple and time-saving expedient of determining the sensitivity of a few selected points of the raster (i.e., of the group of stimulus values).

The modifying step may include replacing the stimulus values of the original group with the corresponding threshold values or altering the stimulus values of the corrected group to an extent such that the altered values are determined at least substantially (e.g., by 50 percent or primarily) by the corresponding freshly ascertained threshold values.

The same procedure can be followed in the course of a third, fourth, etc. perimetric examination, i.e., the group of stimulus values which is presented to the subject during each next-following examination constitutes the group of modified stimulus values stored upon completion of the immediately preceding examination.

It is further within the purview of the invention to proceed as follows: The individual or discrete threshold values which are obtained as a result of actual presentation to the subject are attributed greater significance then the interpolated threshold values and/or those stimulus values of the original group (mean thresholds for the corresponding age group) which were not presented to the subject. This enables the person perusing the record to properly evaluate the results of the last examination with reference to the results of the preceding examination.

The novel features which are considered as characteristic of the invention are set forth in particular in the appended claims. The improved method itself, however, together with additional features and advantages thereof, will be best understood upon perusal of the following detailed description of certain specific embodiments of a perimeter machine with reference to the accompanying drawing.

DESCRIPTION OF THE PREFERRED EMBODIMENTS

Figure 1:
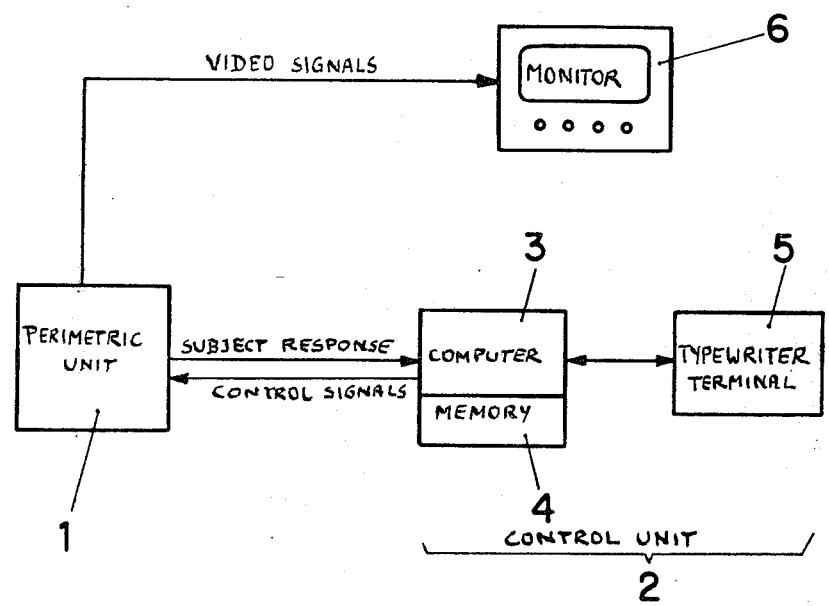
FIG. 1 is a block diagram showing certain constituents of a computerized perimeter machine which can be utilized for the practice of the improved method.

FIG. 1 shows certain constituent parts of an "OCTOPUS" (trademark) perimeter machine. Such parts include a perimetric unit 1 with a customary cupola defining a viewing field and with a spot projector, and a control unit 2. The latter includes a computer 3 (e.g., an Intel MDS microprocessor with random access memory of 32,000 8-bit words) with an external memory 4, preferably a floppy disc device for external storage of programs and results. However, such memory can be replaced with equipment utilizing magnetic tape or the like. The control unit 2 further includes a typewriter terminal 5 which can supply data to or receive and record information from the computer 3. Still further, the control unit 2 includes certain optional components, such as a rotatable monitor 6 which can serve for automatic eye fixation control.

Figure 2:
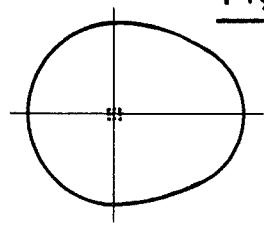
FIG. 2 is a two-dimensional representation of the visual field of an eye, showing the examination program for static perimetry of the center of the visual field.
Figure 3:
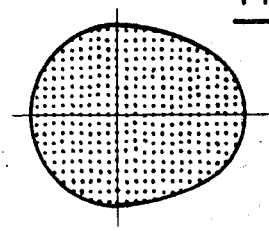
FIG. 3 shows the examination program for static screening perimetry including a general survey of the entire visual field.
Figure 4:
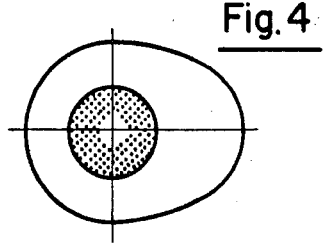
FIG. 4 shows the examination program for static perimetry of the inner area of the visual field between zero and 30 degrees.
Figure 5:
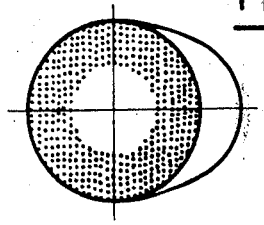
FIG. 5 shows the examination program which is complementary to the program of FIG. 4 and involves static perimetry in the intermediate range of the visual field between 30 and 60 degrees.
Figure 6:
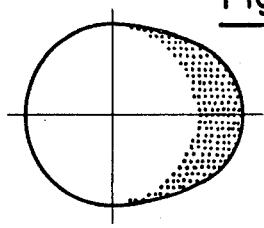
FIG. 6 shows the examination program for static perimetry of the outer range of the visual field between 60 and 90 degrees.
Figure 7:
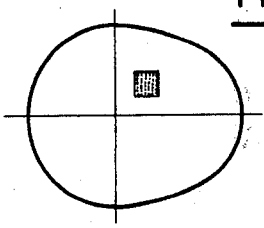
FIG. 7 shows an example of an examination program for static precision perimetry of a selected portion of the visual field.

The eye of a patient who is sitting in front of the cupola of the perimetric unit 1 is presented a raster of stimuli of variable intensity. The raster overlies the visual field which is adequately illuminated in a manner well known from the art of perimeter machines. The presentation of stimuli of varying intensity at selected points or test locations of the raster proceeds until the subject indicates (by way of a suitable subject response device or by a visible or audible signal) the threshold, which has been perceived by his or her eye, for each of a selected group of stimulus values. The program which is selected by the person in charge and communicated to the computer 3 determines the group of stimulus values, i.e., the distribution of those stimulus values which are to be presented to a subject in the course of perimetric examination. The program may involve the center of the visual field (FIG. 2), the entire visual field (FIG. 3), the inner area of the visual field (FIG. 4), the intermediate range of the visual field (FIG. 5), the outer range of the visual field (FIG. 6), or a selected portion of the visual field (FIG. 7).

When examining the entire visual field (FIG. 3), it is normally preferred to select only certain stimuli of a complete group, e.g., each sixth point of the raster. This results in savings in time and suffices, at least in many instances, to complete a preliminary survey of the sensitivity of the subject's eye. When examining in accordance with the program of FIG. 2, 4, 5 or 6, it normally suffices to present each third point of the raster. On the other hand, an examination in accordance with the program of FIG. 7 normally involves the presentation of a stimulus to every point of the raster. The raster is assumed to be located in a plane normal to the direction of gaze.

During the first examination of a subject (in accordance with any of the programs shown in FIGS. 2–7), the subject is properly seated with respect to the cupola of the perimetric unit 1 and is presented a group of stimulus values each of which represents the mean threshold for the age group of the subject. The examination then proceeds, preferably in accordance with the aforediscussed bracketing system. The computer 3 presents at each point stimuli of varying intensity and the subject acknowledges the perception of stimuli including the threshold value of each stimulus. This completes the test.

Figure 8:
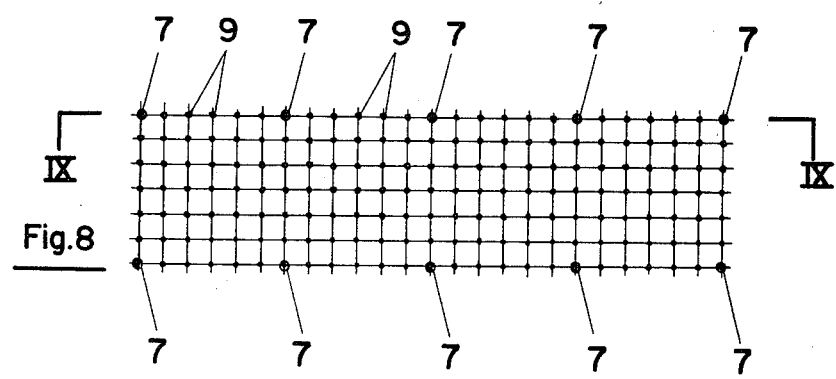
FIG. 8 shows a portion of a lattice-like raster which is placed over the visual field.

FIG. 8 illustrates one mode of a first examination of the visual field of a subject. Such examination is assumed to be carried out with the program of FIG. 3, i.e., the subject is presented a group of stimuli at each sixth point 7 of the raster. As mentioned above, each first stimulus at a point 7 represents the mean threshold for the age group of the subject. Such mean threshold values are represented by the black dots on the curve 8 of FIG. 9. It is assumed that the real (ascertained) thresholds of stimuli at the raster points 7 shown in FIG. 8 are such as indicated by the circles on the curve 10 of FIG. 9, i.e., most measured thresholds do not coincide with the corresponding mean thresholds on the curve 8 of FIG. 9. By comparing the corresponding stimuli on the curves 8 and 10 of FIG. 9, i.e., in the plane denoted by the line IX—IX of FIG. 8, it will be noted that the values of measured thresholds (circles on the line 10) are higher than the mean thresholds for the age group of the subject (dots on the line 8) in the left-hand part of FIG. 9 and lower in the right-hand part of FIG. 9. More particularly, the leftmost measured value 10A is higher than the leftmost mean threshold 8A, the next measured value 10B matches the corresponding mean threshold 8B, the third measured value 10C is less than the mean threshold 8C, and the remaining two measured values 10D, 10E are also less than the corresponding mean thresholds 8D, 8E. The computer 3 interpolates the missing values (points 9) on the curve 10 (the interpolated values are denoted in FIG. 9 by the symbols "x"). The interpolating operation can be carried out in the course of or upon completion of the test.

In accordance with a feature of the invention, the computer 3 thereupon stores, in its own memory, the measured values instead of the corresponding mean thresholds (i.e., the mean thresholds 8A, 8C, 8D, 8E are respectively replaced with the values 10A, 10C, 10D, 10E). In the same way, the interpolated values (marked "x") replace the corresponding mean thresholds. Consequently, the stored modified threshold values are those represented by the curve 10 of FIG. 9. The computer 3 thereupon transfers such information into the external memory 4 which stores the information for use (as a group of stimulus values) for the next-following examination of the visual field of the same subject. Thus, the next-following test is started by presenting to the subject stimulus values which are not identical with mean thresholds for the particular age group but by presenting instead modified stimulus values wherein each mean threshold (save for the mean threshold 8B which is identical with the ascertained threshold 10B) is already replaced with the corresponding value as ascertained in the course of the preceding perimetric examination.

Figure 9:
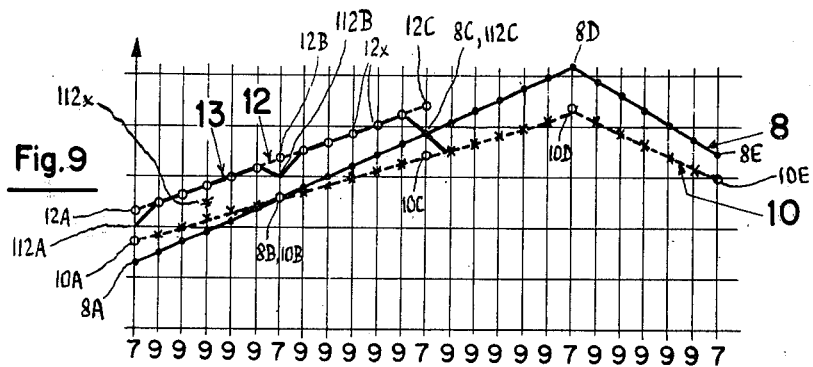
FIG. 9 is a quantitative representation of the measured values along the line IX—IX of FIG. 8 upon completion of two examinations.

It is now assumed that the next-following examination is performed in a manner as represented by the curve 12 of FIG. 9. Thus, the subject is presented each and every stimulus value (curve 10 of FIG. 9) up to the third point 7 of the raster (as considered in a direction from the left to the right). The group of stimulus values represented by the curve 10 must be modified in accordance with the results of the second test. At the points 7 where the values on the curve 10 represent thresholds actually ascertained during the preceding test, the computer 3 calculates the arithmetic mean of the values 10A, 10B and 10C on the one hand and the freshly ascertained threshold values 12A, 12B, 12C on the other hand. The resulting values are shown at 112A, 112B, 112C. At the points 9, where the values represented by the symbols "x" on the curve 10 were obtained by interpolation (i.e., not by actual testing), the values "x" are replaced by threshold values (12x) obtained as a result of actual testing in the course of the second examination. Thus, when the second examination is completed, the computer 3 transmits to the external memory 4 information in the form of a curve 13 which includes the threshold values 112A, 112B, 112C, the values 12x, and the values represented by the right-hand half of the curve 10. Such information constitutes a group of stimulus values for the next-following (third) examination of the same subject. The right-hand half of the curve 10 remains unchanged because the second examination did not involve a testing of the entire visual field.

It is also within the purview of the invention to utilize the computer 3 as a means for replacing the values 12x on the curve 13 with values constituting an arithmetic mean between the values 12x and the corresponding values "x" in the left-hand half of the curve 10. One of the thus modified values "x" is indicated at 112x.

Figure 10:
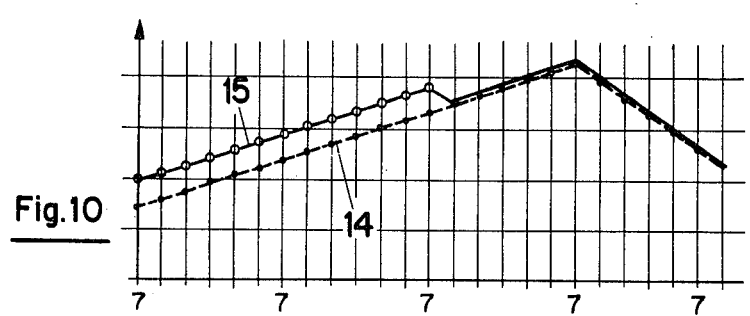
FIG. 10 is a similar quantitative representation of the results of a different examination.

If a first test involves static perimetric examination of a portion of the visual field, such first test is again started by presenting to the subject a group of stimulus values which constitute mean thresholds for the particular age group. i.e., a statistically determined group of stimulus values. As shown in FIG. 10, the first test merely involves the examination at each raster point to the third point 7 (the ascertained thresholds of stimulus values which are presented to the subject are denoted by circles). The curve 14 represents the group of stimulus values constituting the mean thresholds for the particular age group, and the curve 15 represents the information which is stored in the external memory 4 upon completion of the first test. Thus, one-half of the curve 15 represents thresholds which are ascertained in the course of the first test, and the other half of the curve 15 is identical with the corresponding part of the curve 14. It will be noted that the ascertained threshold values replace the mean thresholds but the mean thresholds are retained for that part of the visual field which was not tested during the first perimetric examination. The information which is represented by the curve 15 is used for presentation of a group of stimulus values to the same subject in the course of the next-following test. The data obtained on completion of the second test are stored in the memory 4 for the third test, and such data are obtained in the same way as described in connection with FIG. 9, i.e., the computer 3 calculates the arithmetic mean of two related threshold values which were obtained by actual testing but the computer retains the previous information for each point of the raster which was not examined during the second test.

To summarize: The stimulus values which represent mean thresholds for a particular age group are replaced by thresholds which are ascertained in the course of an actual test, i.e., the modification of mean thresholds involves replacement of such mean thresholds by thresholds obtained as a result of actual testing. On the other hand, if a second test involves testing at the same point of the raster, the computer modifies the previously obtained threshold in view of the freshly obtained threshold by ascertaining the arithmetic mean of such stimuli. In other words, each freshly ascertained threshold carries as much weight as all corresponding previously ascertained thresholds together.

The manner in which the perimeter machine furnishes a visible record of each examination forms no part of the invention. As a rule, static perimetry resorts to one of three presently preferred display techniques, namely, (a) so-called profile sections are made along a meridian through the visual field, (b) in concentric circles around the center of the visual field, or (c) in arbitrary directions. Display by proportional areas (grey tones) is a highly satisfactory technique. In such two-dimensional graphical display, the third component (sensitivity) is presented by dots whose areas are inversely proportional to the sensitivity. Reference may be had to the article entitled "The Automation of Perimetry" by J. Spahr, H. Bebie and F. Frankhauser published by the assignee. A preferred method of graphically displaying the results of repeated automatic perimetric examination of visual fields is disclosed in commonly owned copending application Ser. No. 933,852 filed Aug. 15, 1978.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

I claim:

1. A method of testing the visual field of a subject, comprising the steps of presenting to the subject spots of light constituting a group of initial stimulus values at selected test locations of a test field having a predetermined orientation relative to the direction of gaze of the subject; adjusting stimulus values of the respective spots of light until the threshold values which acted as stimuli to the subject at the respective test locations are ascertained; modifying at least some of the initial stimulus values of said group as a function of the corresponding ascertained threshold values; storing the thus modified stimulus values of said group; and repeating at least said presenting step using said stored values instead of said initial stimulus values during a subsequent test of the same subject.

2. A method as defined in claim 1, wherein said selected group of initial stimulus values constitutes the mean thresholds for the age group of the subject.

3. A method as defined in claim 1, further comprising the steps of interpolating additional stimulus values between the ascertained threshold values and modifying the corresponding initial values of said group as a function of said interpolated stimulus values.

4. A method as defined in claim 1, wherein said modifying step comprises replacing the initial stimulus values of said group by the corresponding ascertained threshold values.

5. A method as defined in claim 1, wherein said modifying step includes altering the initial stimulus values of said group to an extent such that the altered values are pronouncedly influenced by the corresponding ascertained threshold values.

6. A method as defined in claim 5, wherein each altered value constitutes the arithmetic mean of the initial stimulus value of said group and the corresponding ascertained threshold value.

7. A method as defined in claim 1, further comprising the steps of interpolating additional stimulus values between the ascertained threshold values, and modifying the corresponding initial stimulus values of said group as a function of the interpolated stimulus values, said modifying steps including modifying the initial stimulus values of said group to an extent such that the influence of the ascertained threshold values upon the corresponding initial stimulus values is more pronounced than the influence of said interpolated stimulus values upon the corresponding initial stimulus values of said group.

8. A method as defined in claim 1, wherein said repeating step further includes ascertaining the threshold values which acted as stimuli to the subject, and modifying the stored stimulus values as a function of the corresponding ascertained threshold values, including forming an arithmetic mean of the ascertained threshold values and the corresponding stored stimulus values; and wherein said storing step includes storing only said modified stimulus values while retaining those stimulus values of said stored group which were not presented to the subject in the course of said subsequent test.

9. A method as defined in claim 1, wherein said presenting step includes presenting said spots of light for each predetermined stimulus value of said group in accordance with the bracketing system.

10. A method as defined in claim 1, wherein said modifying step takes place simultaneously with said presenting step.

* * * * *